(12) United States Patent
Ebersole et al.

(10) Patent No.: US 11,849,969 B2
(45) Date of Patent: Dec. 26, 2023

(54) CANNULA WITH SMOKE EVACUATION HOUSING

(71) Applicant: Covidien LP, Mansfield, MA (US)

(72) Inventors: Garrett P. Ebersole, Hamden, CT (US); Roy J. Pilletere, Middletown, CT (US); Justin Thomas, New Haven, CT (US); Nicolette L. Roy, Windsor Locks, CT (US); Saumya Banerjee, Hamden, CT (US); Jacob C. Baril, Norwalk, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 173 days.

(21) Appl. No.: 17/111,636

(22) Filed: Dec. 4, 2020

(65) Prior Publication Data
US 2022/0175418 A1 Jun. 9, 2022

(51) Int. Cl.
*A61B 17/34* (2006.01)
*A61B 17/00* (2006.01)

(52) U.S. Cl.
CPC .... *A61B 17/3423* (2013.01); *A61B 17/00234* (2013.01); *A61B 2017/00561* (2013.01); *A61B 2017/3419* (2013.01)

(58) Field of Classification Search
CPC .......... A61B 17/3423; A61B 17/00234; A61B 2017/00561; A61B 2017/3419; A61B 2218/008; A61B 17/3421
See application file for complete search history.

(56) References Cited

U.S. PATENT DOCUMENTS

| 397,060 | A | 1/1889 | Knapp |
| 512,456 | A | 1/1894 | Sadikova |
| 1,213,005 | A | 1/1917 | Pillsbury |
| 2,912,981 | A | 11/1959 | Keough |
| 2,936,760 | A | 5/1960 | Gains |
| 3,039,468 | A | 6/1962 | Price |
| 3,050,066 | A | 8/1962 | Koehn |
| 3,253,594 | A | 5/1966 | Matthews et al. |

(Continued)

FOREIGN PATENT DOCUMENTS

| CN | 107970061 A | 5/2018 |
| EP | 0480653 A1 | 4/1992 |

(Continued)

OTHER PUBLICATIONS

International Search Report and Written Opinion dated Feb. 22, 2022 issued in corresponding PCT Appln. No. PCT/US2021/060262.

*Primary Examiner* — Shaun L David
*Assistant Examiner* — Rachael L Geiger
(74) *Attorney, Agent, or Firm* — Carter, DeLuca & Farrell LLP

(57) ABSTRACT

A surgical access device includes a cannula and a seal housing. The cannula has a cannula housing and a tubular member that extends from the cannula housing. The seal housing is coupled to the cannula housing. The seal housing has a base and a cover with an instrument seal located between the base and the cover. The cover has an upper cover portion and a lower cover portion with a port extending from the upper cover portion. The port is connectable to a source of vacuum. A chamber with projections and windows is defined in the upper cover portion and is configured to direct fluid towards the port.

20 Claims, 6 Drawing Sheets

(56) References Cited

U.S. PATENT DOCUMENTS

| | | |
|---|---|---|
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Ander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 7,300,448 B2 | 11/2007 | Criscuolo et al. |
| 7,691,089 B2 | 4/2010 | Gresham |
| 8,454,645 B2 | 6/2013 | Criscuolo et al. |
| 8,926,508 B2 | 1/2015 | Hotter |
| 10,022,149 B2 | 7/2018 | Holsten et al. |

(56) References Cited

U.S. PATENT DOCUMENTS

| | | | |
|---|---|---|---|
| 2007/0088274 A1 | 4/2007 | Stubbs et al. | |
| 2009/0270818 A1 | 10/2009 | Duke | |
| 2010/0214061 A1 | 8/2010 | Twitchell, Jr. et al. | |
| 2014/0336634 A1 | 11/2014 | Gomez | |
| 2018/0228510 A1* | 8/2018 | Holsten | A61B 17/3474 |
| 2020/0305928 A1* | 10/2020 | Thompson | A61B 17/00234 |

FOREIGN PATENT DOCUMENTS

| | | |
|---|---|---|
| EP | 0610099 A2 | 8/1994 |
| EP | 0880939 A1 | 12/1998 |
| EP | 1188415 A2 | 3/2002 |
| EP | 3360494 A1 | 8/2018 |
| KR | 102112026 B1 | 5/2020 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2016186905 A1 | 11/2016 |

* cited by examiner

CANNULA WITH SMOKE EVACUATION HOUSING

FIELD

The present disclosure generally relates to surgical instruments for accessing a surgical site in a patient. In particular, the present disclosure relates to a cannula having a smoke evacuation housing.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the minimally invasive surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula into the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an anchor to prevent the cannula from backing out of the opening in the abdominal wall, for example, during withdrawal of the laparoscopic instrument from the cannula. In some procedures, electrosurgical instruments are employed leading to smoke and particulate generation. The smoke and particulate matter needs to be removed while the cannula remains positioned in body tissue.

SUMMARY

In an aspect of the present disclosure, a surgical access device includes a cannula having a cannula housing at a proximal end thereof and a tubular member extending from the cannula housing. A seal housing is coupled to the cannula housing. The seal housing includes a base attached to the cannula housing, an instrument seal, and a cover having a port extending therefrom. The cover has a lower cover portion and an upper cover portion. The lower cover portion is attached to the base and the upper cover portion has a chamber therein. The chamber includes projections wherein adjacent projections are spaced apart defining windows therebetween. The windows and the projections define a geometry of the chamber that is configured to direct a fluid in the seal housing towards the port. The port is connectable to a source of vacuum.

In one aspect, a vacuum may be present in the port that creates a flow path in the chamber that directs the fluid in the seal housing towards the port.

In another aspect, a wall of the cover may define the chamber and a passage may be defined between the wall and the projections.

In aspects, the fluid entering the seal housing may pass through the windows into the passage and may be directed towards the port.

In an aspect, the projections, the windows, and the passage may define the geometry of the chamber and may facilitate flow towards the port.

In a further aspect, the upper cover portion may have an arm depending therefrom and the lower cover portion may have a finger that cooperate to align the upper cover portion and the lower cover portion for assembly.

In aspects, the seal housing may be releasably coupled to the cannula housing.

In yet another aspect, the fluid entering the seal housing may pass through the windows into the passage and a vacuum present in the port may direct the fluid towards the port.

In an aspect, the fluid may travel through the tubular member and into the seal housing.

In a further aspect of the present disclosure, a surgical access device has a cannula and a seal housing. The cannula includes a cannula housing and a tubular member extending therefrom. The seal housing includes a base attachable to the cannula, an instrument seal, and a cover having a lower cover portion and an upper cover portion. The lower cover portion is attached to the base and the upper cover portion is connectable with the lower cover portion. The upper cover portion has a wall depending therefrom and defines a chamber. The chamber includes projections depending from the upper cover portion. The projections are spaced apart and define windows therebetween. A port extends radially from the upper cover portion. A passage is defined between a surface of the wall and the projections. The projections, the windows, and the passage define a geometry of the chamber that is configured to direct a fluid in the seal housing towards the port that is connectable to a source of vacuum.

In an aspect, a vacuum present in the port may create a flow path in the chamber that directs the fluid in the seal housing towards the port.

In another aspect, the fluid entering the seal housing may pass through the windows into the passage and may be directed towards the port.

In aspects, the upper cover portion may have an arm depending therefrom and the lower cover portion may have a finger that cooperate to align the upper cover portion and the lower cover portion for assembly.

In one aspect, the seal housing may be releasably coupled to the cannula housing.

In another aspect, the fluid may travel through the tubular member and into the seal housing.

In yet another aspect of the present disclosure, a method of removing fluid from a surgical access device includes connecting a source of vacuum to a surgical access device. The surgical access device has a cannula with a cannula housing and a tubular member extending therefrom. A seal housing is coupled to the cannula housing. The seal housing includes a base, an instrument seal, and a cover having a port extending therefrom. The cover has a lower cover portion attached to the cannula housing and an upper cover portion.

The upper cover portion has a chamber therein. The chamber includes projections wherein adjacent projections are spaced apart defining windows therebetween. The windows and the projections define a geometry of the chamber. The method also includes applying a vacuum to the chamber via the port. The vacuum and the geometry of the chamber creating a flow path in the seal housing that directs a fluid in the seal housing towards the port.

In one aspect, applying the vacuum to the chamber via the port may direct the fluid entering the chamber towards a wall of the chamber.

In another aspect, applying the vacuum to the chamber via the port may direct the fluid entering the chamber through the windows and into a passage defined between the projections and the wall.

In aspects, applying the vacuum to the chamber via the port may cause the fluid to travel through the tubular member and into the seal housing.

In a further aspect, connecting the source of vacuum to the surgical access device may include the seal housing being removably coupled to the cannula housing.

Other features of the disclosure will be appreciated from the following description.

DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
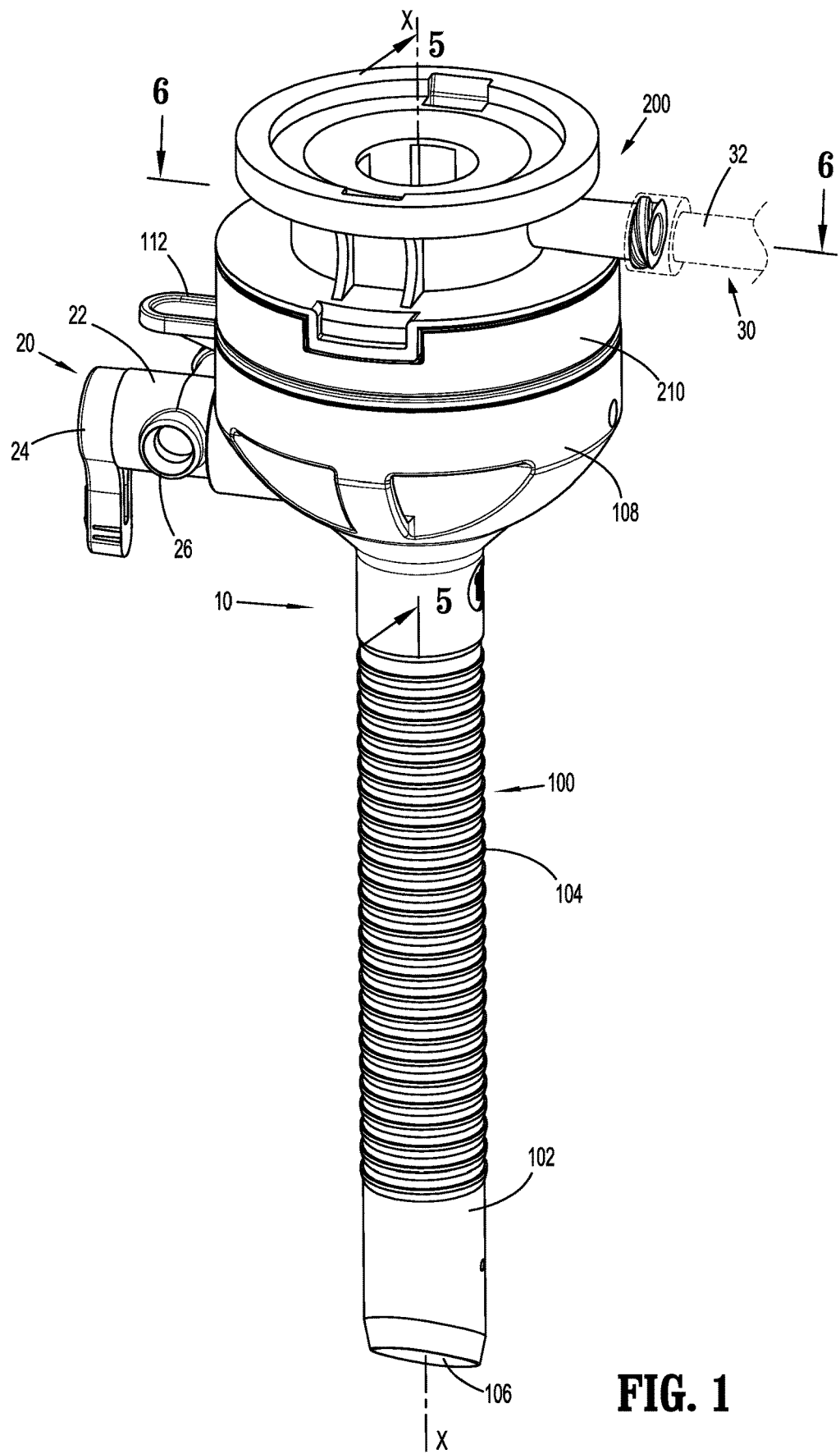
FIG. 1 is a perspective view of a surgical access device according to an aspect of the present disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an aspect of the disclosure should typically be considered as available and applicable to other similar features of another aspect of the disclosure. Accordingly, technical features described herein according to one aspect of the disclosure may be applicable to other aspects of the disclosure, and thus duplicative descriptions may be omitted herein. Like reference numerals may refer to like elements throughout the specification and drawings. For a detailed description of the structure and function of exemplary surgical access assemblies, reference may be made to commonly owned U.S. Pat. Nos. 7,300,448; 7,691,089; and 8,926,508, the entire content of each of which is hereby incorporated by reference herein.

Figure 2:
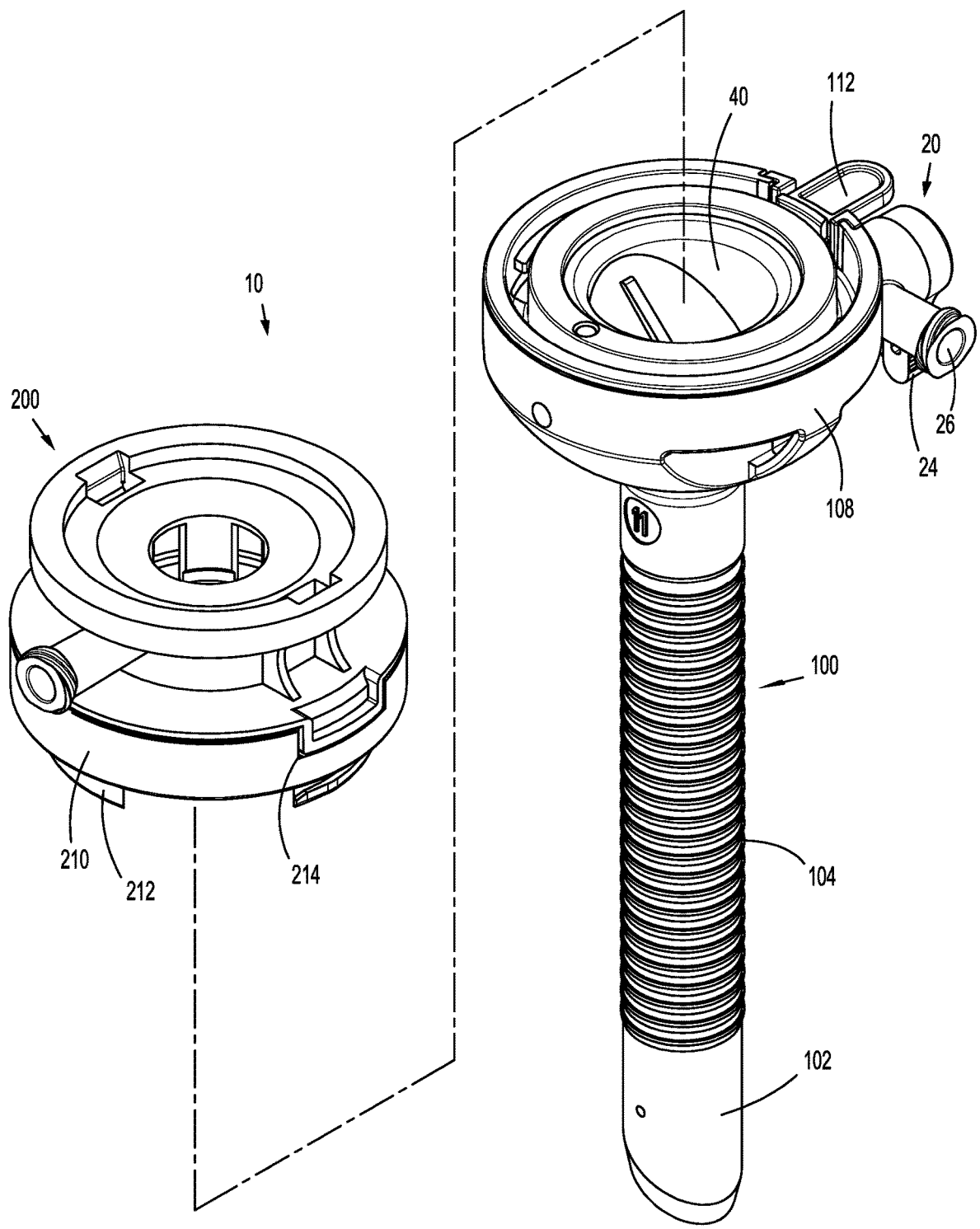
FIG. 2 is an exploded perspective view, with parts separated, of the surgical access device of FIG. 1.
Figure 3:
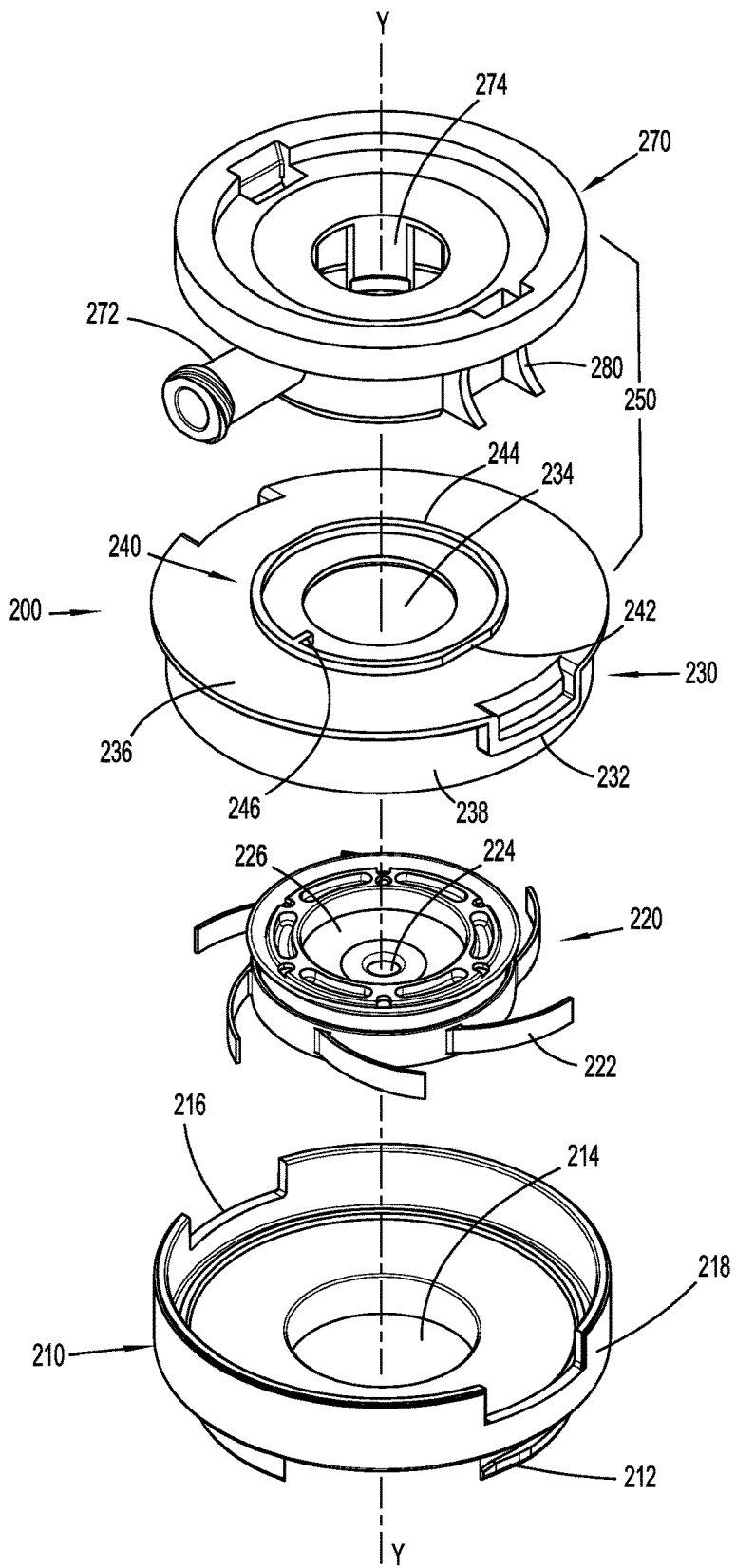
FIG. 3 is an exploded perspective view, with parts separated, of a seal housing of the surgical access device of FIGS. 1 and 2.

With initial reference to FIGS. 1-3, a surgical access device according to an aspect of the present disclosure is shown generally as surgical access device 10. The surgical access device 10 includes a cannula 100 and a seal housing 200 coupled to the cannula 100. The cannula 100 has a cannula housing 108 and a tubular member 102 extending from the cannula housing 108. A longitudinal axis X-X extends through the surgical access device 10. The tubular member 102 may include ribs or other protrusions 104 along a portion of its length that help stabilize the cannula 100 when it is inserted into tissue. The tubular member 102 further includes a lumen 106 that is configured to receive a surgical instrument, such as an obturator, endoscopic stapler, an electrosurgical instrument, etc., (not shown) therein. Additionally, the cannula housing 108 has a valve 20 extending radially therefrom. The valve includes a body 22, a handle 24, and a valve port 26. The handle 24 is rotatable relative to the body 22 such that a first position of the handle 24 defines an open configuration of the valve 20 that allows fluid to flow through the valve 20 and a second position of the handle 24 defines a closed configuration of the valve 20 that inhibits fluid from flowing through the valve 20. The valve 20 may be a stop cock valve. The cannula housing 108 also includes a duckbill or zero-closure valve 40. The cannula housing 108 and the tubular member 102 are formed from a suitable biocompatible polymeric material (e.g., polycarbonate).

The seal housing 200 includes an instrument seal 220 positioned in the seal housing 200 and includes a central opening 224 that sealingly engages a surgical instrument (not shown) inserted through a channel of the seal housing 200. When a surgical instrument is inserted through the central opening 224, it is engaged with the instrument seal 220 and the instrument seal 220 provides a fluid-tight barrier. The seal housing 200 is formed from a suitable biocompatible polymeric material (e.g., polycarbonate).

The base of the seal housing 200 is releasably attached to the cannula housing 108. A tab 112 extends radially from the cannula housing 108 and is configured for resilient movement relative thereto such that the tab 112 is movable in a distal direction relative to the cannula housing 108. Moving the tab 112 distally permits a user to rotate the seal housing 200 relative to the cannula housing 108 for removal of the seal housing 200 from the surgical access device 10. Attachment of the seal housing 200 to the cannula housing 108 of the surgical access device 10 involves rotating the seal housing 200 relative to the cannula housing 108 in an opposite direction. An example of a seal housing, including an instrument seal, attachable to a housing of a surgical access device is described in commonly owned U.S. Pat. No. 10,022,149, the entire content of which is incorporated herein by reference.

With continued reference to FIG. 3, the seal housing 200 includes a base 210 and a cover 250. The base 210 has a circular frame 218 with prongs 212 depending therefrom that align with complimentary features of the cannula housing 108 for coupling the base 210 to the cannula housing 108. The cover 250 has a lower cover portion 230 and an upper cover portion 270. The lower cover portion 230 has a circular frame 238 and a top surface 236. The instrument seal 220 is disposed within the seal housing 200 and is positioned between the lower cover portion 230 and the base 210. The instrument seal 220 includes spokes 222 that facilitate maintaining the instrument seal 220 centered in the seal housing 200 in the absence of a surgical instrument inserted therethrough. Additionally, the instrument seal 220 includes a membrane having the central opening 224 for slidably receiving a surgical instrument therethrough. In the absence of a surgical instrument, the central opening 224 is coincident with axis Y-Y. The base 210, the lower cover portion 230, and the upper cover portion 270 include respective coaxial central openings 214, 234, 274 that are coincident with axis Y-Y and are aligned with axis X-X of the surgical access device 10. The lower cover portion 230 has tabs 232 that complement notches 216 in the base 210 for aligning and orienting the lower cover portion 230 and the base 210 during assembly. The lower cover portion 230 may be joined to the base 210 using various techniques including, but not limited to, friction fit, adhesives, ultrasonic welding, etc. Additionally, the top surface 236 of the lower cover portion 230 has a raised rib 240 that generally circumscribes the central opening 234 of the lower cover portion 230. The rib 240 includes opposed arcuate sections 244 separated by opposed linear sections 242. The linear sections 242 are generally parallel to the tabs 232 of the lower cover portion 230. One of the arcuate sections 244 has a finger 246 extending therefrom along the top surface 236 towards the central opening 234 of the lower cover portion 230. The finger 246 and the linear sections 242 cooperate with the upper cover portion 270 for aligning the upper and lower cover portions 270, 230 during assembly as will be discussed hereinafter. Although shown as extending from one of the arcuate sections 244, the finger 246 may be disposed on one of the linear sections 242. Further, the upper cover portion 270 includes a port 272 extending radially from the upper cover portion 270. As shown in FIG. 1, the port 272 is attachable to a source of vacuum 30 through tube 32. The upper cover portion 270 includes projections 264 extending from an inner surface thereof.

Figure 4:
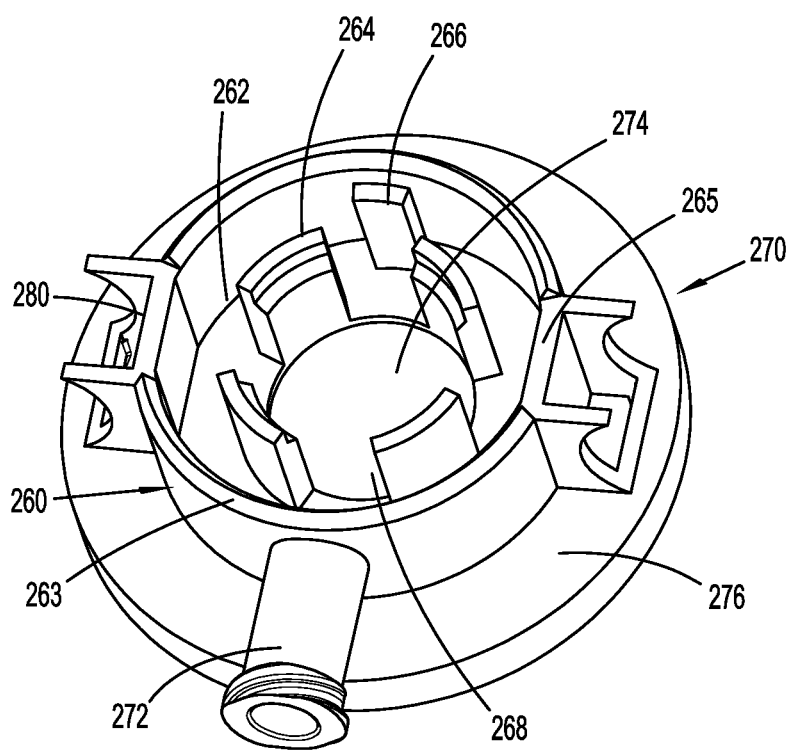
FIG. 4 is a bottom perspective view of a cover portion of the seal housing of FIG. 3.
Figure 5:
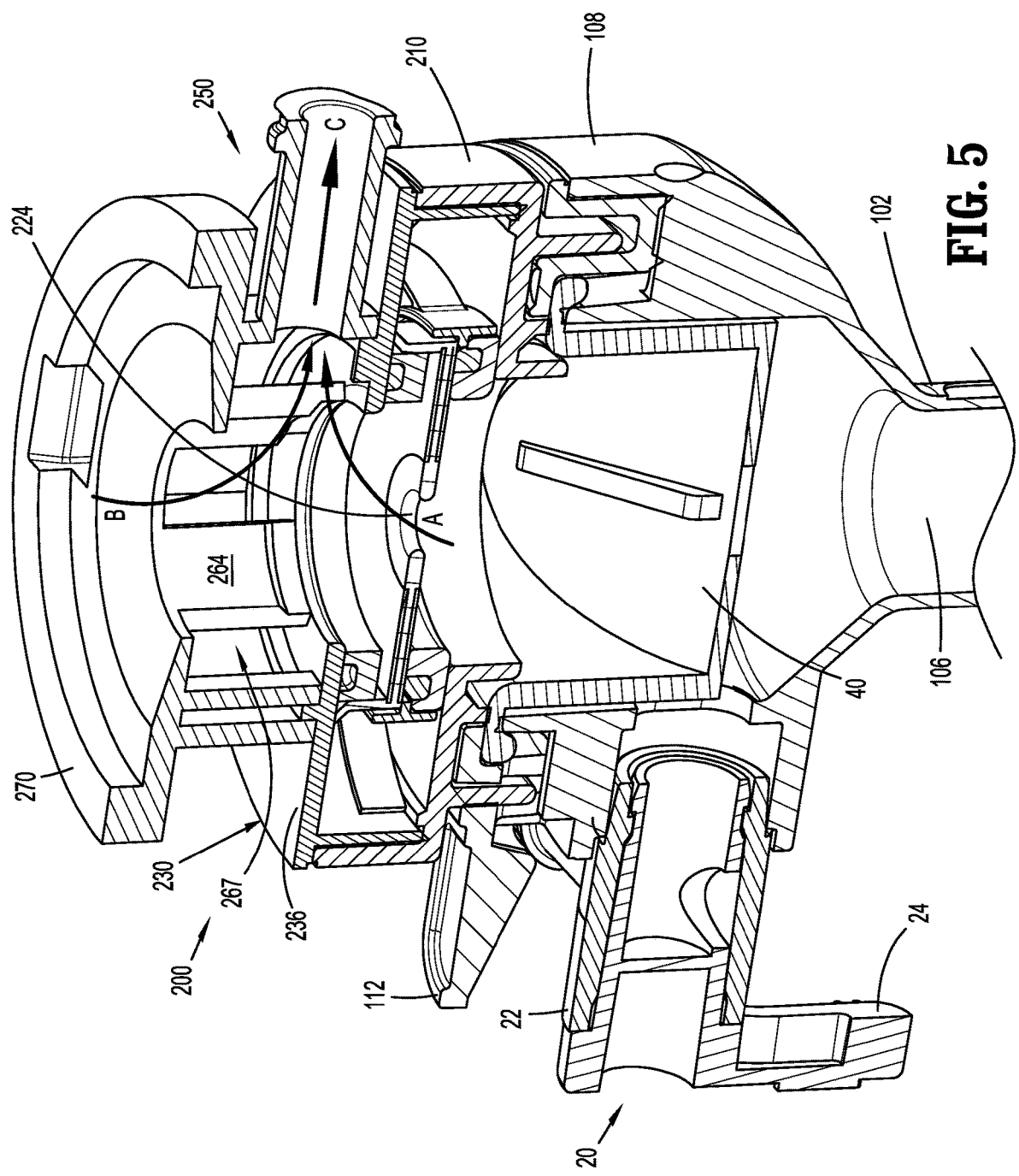
FIG. 5 is a side cross-sectional view of a proximal region of the surgical access device taken along section line 5-5 of FIG. 1.
Figure 6:
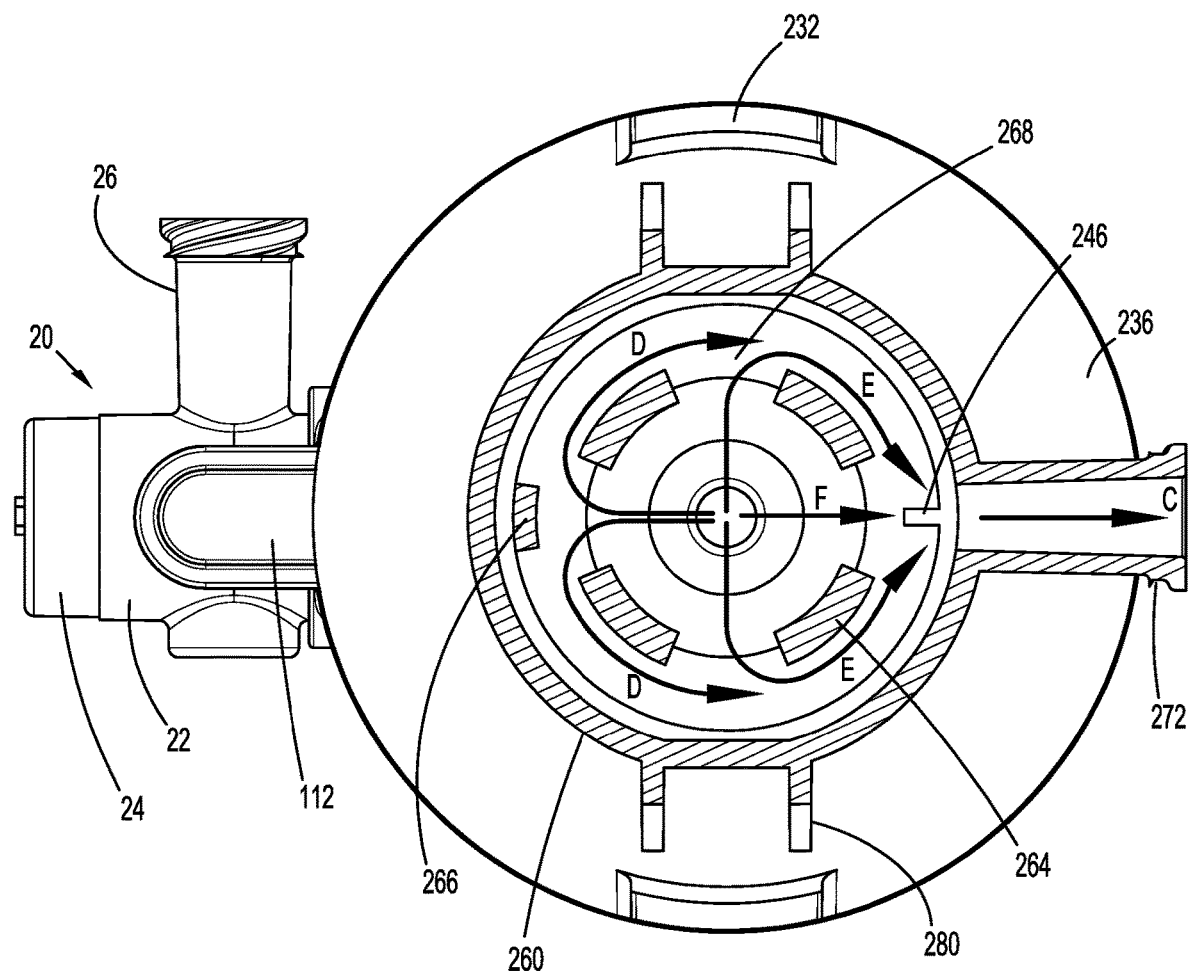
FIG. 6 is a top cross-sectional view of the surgical access device taken along section line 6-6 of FIG. 1.

With additional reference to FIGS. 4 and 6, alignment and assembly of the cover 250 is illustrated. Initially, as seen in FIG. 4, an underside of the upper cover portion 270 has a wall 260 depending therefrom. The wall 260 defines a chamber 262 that surrounds the central opening 274 of the upper cover portion 270. Additionally, a passage 267 (FIG. 5) is defined between an inner surface of the wall 260 and the projections 264. The passage 267, in combination with the projections 264, the windows 268, define a geometry of the chamber 262 that is configured to facilitate fluid flow towards the port 272. The wall 260 has opposed arcuate sections 263 connected by opposed linear sections 265. The arcuate and linear sections 263, 265 of the wall 260 correspond to the arcuate and linear sections 244, 242 of the rib 240 disposed on the lower cover portion 230. The rib 240 of the lower cover portion 230 fits within the perimeter of the wall 260 as shown in FIG. 6 such that an outer surface of the rib 240 engages an inner surface of the wall 260 (i.e., flush fit). In particular, the arcuate sections 263 of the wall 260 align with the arcuate sections 244 of the rib 240 while the linear sections 265 of the wall 260 align with the linear sections 242 of the rib 240 thereby aligning the upper and lower cover portions 270, 230 during assembly and inhibiting rotation of the upper and lower cover portions 270, 230 relative to one another. The linear sections 265 of the wall 260 have struts 280 extending radially therefrom. As with the linear sections 265 of the wall 260, the struts 280 are aligned with the tabs 232 of the lower cover portion 230. An arm 266 extends from the underside of the upper cover portion 270 and is located diametrically opposed the port 272. The arm 266 has a length such that when the upper cover portion 270 and the lower cover portion 230 are attached to each other, a distal end of the arm 266 contacts the top surface 236 of the lower cover portion 230. Similarly, when the upper cover portion 270 is attached to the lower cover portion 230, distal ends of the projections 264 contact the top surface 236 of the lower cover portion 230. Since the upper cover portion 270 and the lower cover portion 230 have complementary arcuate sections 263, 244 and complimentary linear sections 265, 242, the upper cover portion 270 is only attachable to the lower cover portion 230 in one of two possible orientations. However, one of those two possible orientations aligns the arm 266 of the upper cover portion 270 with the finger 246 of the rib 240 of the lower cover portion 230. Contact between the arm 266 and the finger 246 prevent the upper cover portion 270 from sitting flush on the top surface 236 of the lower cover portion 230. Rotating the upper and lower cover portions 270, 230 180° relative to one another positions the arm 266 and the finger 246 in an opposed relationship allowing the upper cover portion 270 to sit flush on the top surface 236 of the lower cover portion 230. This arrangement provides proper alignment and orientation between the upper and lower cover portions 270, 230.

With additional reference to FIG. 5, the central opening 274 of the upper cover portion 270 is circumscribed by the projections 264 that depend from the underside of the upper cover portion 270 and are included in the chamber 262. The projections 264 are arranged such that a window 268 is defined between adjacent projections 264. As illustrated, the upper cover portion 270 has four projections 264 and four windows 268. It is contemplated that the upper cover portion 270 may include more projections 264 and windows 268 or may include fewer projections 264 and windows 268 while still maintaining the functionality of the seal housing 200. Each projection 264 is generally arcuate (i.e., concave inner face and convex outer face) and includes a ledge disposed on an inside surface thereof. The ledge is located near a distal end of the projection 264. Further, although illustrated as having a common configuration, it is contemplated that each projection 264 may have a unique configuration that cooperates with the windows 268 and the wall 260 defining the chamber 262 to define a flow path from a central region of the chamber 262 towards the port 272. This encompasses fluids entering the chamber 262 from the lumen 106 of the tubular member 102 of the cannula 100 through the central opening 224 of the instrument seal 220 as shown by arrow A and the central opening 274 of the upper cover portion 270 as shown by arrow B. It is contemplated that the fluid flow indicated by arrows A and B may be most of the fluid flow from the surgical access device 10 towards the port 272.

With reference now to FIGS. 5 and 6, the flow path through the seal housing 200 is illustrated. In conjunction with a vacuum (i.e., a negative pressure) applied to the port 272 of the upper cover portion 270 as indicated by arrow C, fluid (e.g., gas or liquid) along with any entrained particulate (e.g., smoke) enters the seal housing 200 from the cannula housing 108 as indicated by arrow A and/or from the ambient environment surrounding the surgical access device 10 as indicated by arrow B. Regardless of whether fluid enters the seal housing 200 from the cannula housing 108 or the ambient environment, the fluid flows into a cavity defined by the projections 264 and associated windows 268. From there, a portion of the fluid flows away from the port 272 and through the window 268 opposite the port 272 as indicated by arrows D. Additionally, another portion of the fluid enters the cavity and exits through windows 268 that are transversely oriented to the port 272 as indicated by arrows E. Further still, another portion of the fluid enters the cavity and flows through a window 268 most proximate to the port 272 and towards the port 272 as indicated by arrow F. The configuration of the projections 264 and the windows 268 in combination with the geometry of the chamber 262 determine the relative amounts of fluid flow indicated by arrows D, E, and F.

It is further contemplated that one or more of the projections 264 may have a specific profile. As a result, one or more of the windows 268 may also have a specific profile. These profiles in combination with the chamber 262 defined by the wall 260 of the upper cover portion 270 enhance fluid flow through the seal housing 200 and facilitate removal of fluids including smoke from the surgical access assembly 100 via the port 272.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical access device comprising:
   a cannula having a cannula housing and a tubular member extending from the cannula housing; and
   a seal housing coupled to the cannula housing, the seal housing including:
      a base attached to the cannula housing,
      an instrument seal, and
      a cover having a port, the cover having a lower cover portion and an upper cover portion attached to the lower cover portion, the lower cover portion attached to the base, the upper cover portion including projections contacting an upper surface of the lower cover portion, a wall, and windows defined between adjacent projections, the projections and the wall circumscribing a central opening of the upper cover portion, the wall radially spaced from the projections and defining a chamber between the wall and the projections, wherein the windows and the projections define a geometry of the chamber that is configured to direct a fluid in the seal housing towards the port, the port being connectable to a source of vacuum.

2. The surgical access device of claim 1, wherein a vacuum present in the port creates a flow path in the chamber that directs the fluid in the seal housing towards the port.

3. The surgical access device of claim 1, wherein the fluid entering the seal housing passes through the windows into the chamber and is directed towards the port.

4. The surgical access device of claim 1, wherein the upper cover portion has an arm and the lower cover portion has a finger that cooperate to align the upper cover portion and the lower cover portion for assembly.

5. The surgical access device of claim 1, wherein the seal housing is releasably coupled to the cannula housing.

6. The surgical access device of claim 1, wherein the fluid entering the seal housing passes through the windows into the chamber and a vacuum present in the port directs the fluid towards the port.

7. The surgical access device of claim 6, wherein the fluid travels through the tubular member and into the seal housing.

8. A surgical access device comprising:
   a cannula having a cannula housing and a tubular member; and
   a seal housing including:
      a base attachable to the cannula,
      an instrument seal,
      a cover having a lower cover portion and an upper cover portion, the lower cover portion attached to the base and the upper cover portion connectable with the lower cover portion, the upper cover portion having a wall and projections, the wall radially spaced from the projections defining a chamber between the wall and the projections, the projections spaced apart and defining windows between adjacent projections, the projections in contact with an upper surface of the lower cover portion, and
      a port extending radially from the upper cover portion, wherein the projections and the windows define a geometry of the chamber that is configured to direct a fluid in the seal housing towards the port, the port being connectable to a source of vacuum.

9. The surgical access device of claim 8, wherein a vacuum present in the port creates a flow path in the chamber that directs the fluid in the seal housing towards the port.

10. The surgical access device of claim 8, wherein the fluid entering the seal housing passes through the windows into the chamber and is directed towards the port.

11. The surgical access device of claim 8, wherein the upper cover portion has an arm and the lower cover portion has a finger that cooperate to align the upper cover portion and the lower cover portion for assembly.

12. The surgical access device of claim 8, wherein the seal housing is releasably coupled to the cannula housing.

13. The surgical access device of claim 10, wherein the fluid travels through the tubular member and into the seal housing.

14. A method of removing fluid from a surgical access device comprising:
   connecting a source of vacuum to a surgical access device, the surgical access device including:
      a cannula having a cannula housing and a tubular member; and
      a seal housing coupled to the cannula housing, the seal housing including:
         a base,
         an instrument seal, and
         a cover having a port, the cover having a lower cover portion attached to the base and an upper cover portion attached to the lower cover portion, the upper cover portion having a wall and projections defining a chamber between the wall and the projections, the projections contacting an upper surface of the lower cover portion, wherein adjacent projections are spaced apart defining windows between the adjacent projections, the windows and the projections defining a geometry of the chamber; and
   applying a vacuum to the chamber via the port, the vacuum and the geometry of the chamber creating a flow path in the seal housing, the flow path directing a fluid in the seal housing towards the port.

15. The method of claim 14, wherein applying the vacuum to the chamber via the port directs the fluid entering the chamber towards a wall of the chamber.

16. The method of claim 15, wherein applying the vacuum to the chamber via the port directs the fluid entering the chamber through the windows.

17. The method of claim 14, wherein applying the vacuum to the chamber via the port causes the fluid to travel through the tubular member and into the seal housing.

18. The method of claim 14, wherein connecting the source of vacuum to the surgical access device includes the seal housing being removably coupled to the cannula housing.

19. The surgical access device of claim 8, wherein the wall and the projections circumscribe a central opening of the upper cover portion.

20. The surgical access device of claim 1, wherein the instrument seal is disposed between the lower cover portion and the base.

\* \* \* \* \*